United States Patent [19]

Buckley et al.

[11] 4,263,424
[45] Apr. 21, 1981

[54] ANTI-FUNGAL AND ANTI-BACTERIAL POLYURETHANES

[75] Inventors: Alan J. Buckley; Michael Singer; James H. Wild, all of Manchester, England

[73] Assignee: Imperial Chemical Industries Limited, London, England

[21] Appl. No.: 954,919

[22] Filed: Oct. 26, 1978

[30] Foreign Application Priority Data

Nov. 3, 1977 [GB] United Kingdom ............... 45746/77

[51] Int. Cl.³ ............................................. C08G 18/38
[52] U.S. Cl. ..................................... 528/85; 252/394; 260/45.9 E; 528/288
[58] Field of Search ....................... 260/45.9 E; 528/85

[56] References Cited

U.S. PATENT DOCUMENTS 3,245,962 4/1966 Fischer ................................... 528/85
4,054,676 10/1977 Weinshenker et al. ....... 260/45.95 E

FOREIGN PATENT DOCUMENTS 1057131 2/1967 United Kingdom .

OTHER PUBLICATIONS

Jour. Medicinal Chemistry, 1974, vol. 17, No. 9, pp. 977–981. (Clark et al.).

*Primary Examiner*—H. S. Cockeram
*Attorney, Agent, or Firm*—Cushman, Darby & Cushman

[57] ABSTRACT

Polyurethane polymers having the general formula:

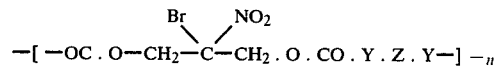

wherein each Y is an —NH— group, Z is an optionally substituted divalent hydrocarbon radical and n is an integer of at least 2; their preparation by reacting 2-bromo-2-nitropropane-1,3-diol and a diisocyanate $Z(NCO)_2$ and the use of the polymers for the protection of various media against attack by microorganisms.

9 Claims, No Drawings

ANTI-FUNGAL AND ANTI-BACTERIAL POLYURETHANES

This invention relates to polymers and more particularly to polymeric biocides.

The compound 2-bromo-2-nitropropane-1,3-diol is known to have antibacterial and antifungal activity, for example, as disclosed in United Kingdom Patent specification No. 1057131. It has now been found that polymers derived from 2-bromo-2-nitropropane-1,3-diol also have biocidal activity and have the advantage over the diol of greater stability, lower toxicity and also that it is possible specifically to tailor the physical properties of polymers according to their intended end use.

According to the present invention there are provided polymers having the general formula:

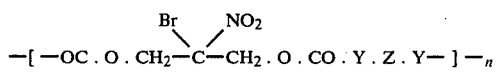

wherein each Y is either a direct link or an —NH— group, Z is an optionally substituted divalent hydrocarbon radical and n- is an integer of at least 2.

The hydrocarbon radical represented by Z may be of the alkylene, cycloalkylene, arylene, alkylarylene, arylalkylene, alkylarylalkylene or arylalkylarylene, specific examples being ethylene, propylene, trimethylene, tetramethylene, pentamethylene, hexamethylene, phenylene, tolylene-2,4- and 2,6-, chlorophenylene, p-$C_6H_4CH_2C_6H_4$-p, cyclohexylene-1,4-$CH_2C_6H_4$-p, —$CH_2CH_2C_6H_4$-p, p-$C_6H_4CH_2$— and p-$C_6H_4CH_2CH_2$—.

According to a further feature of the invention there is provided a process for the manufacture of the polymers as hereinbefore defined wherein each Y is an —NH— group which comprises reacting together 2-bromo-2-nitropropane-1,3-diol and a diisocyanate Z(NCO)$_2$ wherein Z has the meaning defined above.

The reaction is carried out by methods well known in the polyurethane art, and it is preferred to use the diol in slight molar excess over the diisocyanate so that the resulting polymer has hydroxyl rather than isocyanate end groups.

Examples of suitable diisocyanates are aliphatic diisocyanates such as hexamethylene diisocyanate, tetramethylene diisocyanate, 2,2,4- and 2,4,4,-trimethyl hexamethylene diisocyanates, aromatic diisocyanates such as tolylene-2,4-diisocyanate, tolylene-2,6-diisocyanate, diphenylmethane-4,4'-diisocyanate, 3-methyldiphenylmethane-4,4'-diisocyanate, m- and p-phenylene diisocyanate, chlorophenylene-2,4-diisocyanate, xylylene diisocyanate, naphthalene-1,5-diisocyanate, diphenyl-4,4'-diisocyanate, 4,4'-diisocyanato-3,3'-dimethyldiphenyl and diphenyl ether diisocyanate and cycloaliphatic diisocyanates such as dicyclohexylmethane diisocyanates, methylcyclohexylene diisocyanates and 3-isocyanatomethyl-3,5,5-trimethylcyclohexyl isocyanate. Examples of other suitable organic diisocyanates include the reaction products of an excess of a diisocyanate with simple diols e.g. ethylene glycol, 1,4- 1,3- and 2,3- butanediols, diethylene glycol, dipropylene glycol, pentamethylene glycol, hexamethylene glycol, neopentylene glycol, propylene glycol, and with low molecular weight reaction products of the above diols with ethylene oxide and/or propylene oxide.

If desired small proportions of tri- or higher isocyanates, e.g. aromatic triisocyanates such as 2,4,5-triisocyanatotoluene and triisocyanatodiphenylether, may be used together with the diisocyanate, in which case branched polymers will be obtained. Mixtures of diisocyanates may be used.

The invention also comprises co-polymers obtained by reacting 2-bromo-2-nitropropane-1,3-diol and one or more other diols with the diisocyanate. Examples of other diols which may be used in the preparation of such copolymers are ethylene glycol, propylene glycol, trimethylene glycol, 1,4- 1,3- and 2-3-butanediols, diethylene glycol, dipropylene glycol, hexamethylene glycol, neopentylene glycol and 2,2'-dihydroxydiethylsulphide.

The reaction between the 2-bromo-2-nitropropane-1,3-diol (and other diol or diols if used) and the diisocyanate is preferably carried out in a solvent which is inert to isocyanate groups. Suitable solvents are essentially anhydrous esters, ketones, hydrocarbons, halogenated hydrocarbons and amides, for example, urethane grades of ethyl acetate, butyl acetate, methyl ethyl ketone, methyl isobutyl ketone, 4-methoxy-4-methylpentan-2-one, toluene, xylene, trichloroethylene, dimethylformamide and dimethylacetamide. The reaction may be carried out at room temperature or at a moderately elevated temperature, for example, up to 90° C. or even higher, and the progress of the reaction may be followed by measuring the isocyanate content and/or the viscosity of the reaction mixture at intervals. If the reaction is not to be allowed to proceed to completion, i.e. it is to be stopped when a particular viscosity and/or isocyanate content has been reached, the reaction may be terminated by addition of an isocyanate-reactive compound to the reaction mixture, suitable compounds for this purpose being lower aliphatic alcohols such as methanol, glycols such as ethylene glycol or propylene glycol, and alkanolamines such as monoethanolamine and monoisopropanolamine.

The reaction between the 2-bromo-2-nitropropane-1,3-diol and the diisocyanate is preferably carried out in the presence of a catalyst of the kind which accelerates the reaction between an isocyanate group and a hydroxyl group. Examples of such catalysts are organic and inorganic basic compounds, and soluble organic compounds of metals, for example, of transition metals, such as iron and manganese acetylacetonate, and of tin and antimony, for example, stannous octoate and dibutyl tin dilaurate, and compounds of lead such as lead acetate, basic lead acetate and lead 2-ethylhexoate. As basic organic catalysts tertiary amines are suitable, particularly 4-dimethylaminopyridine, triethylenediamine, dimethylbenzylamine and dimethylcyclohexylamine. Mixtures of catalysts may be used, especially mixtures of metal-containing and amine catalysts. The polymer may be isolated from the reaction mixture by conventional means. If the polymer separates out from the reaction mixture then it may be separated from the solvent by decantation or by filtration, followed by further purification of the polymer if desired. If the polymer remains in solution it may be precipitated by addition to the reaction mixture of a solvent which is miscible with the solvent in which the reaction was carried out but in which the polymer is insoluble. Alternatively the solvent may be distilled off from the reaction mixture, if desired under reduced pressure, leaving the polymer as a residue which may be subjected to a purification treatment or treatments if desired.

According to a yet further feature of the invention there is provided a process for the manufacture of the polymers as hereinbefore defined in which each Y is a direct link which comprises esterifying 2-bromo-2-nitropropane-1,3-diol with a dicarboxylic acid.

Examples of suitable dicarboxylic acids are succinic, glutaric, adipic, suberic, azelaic, sebacic, phthalic, isophthalic and terephthalic acids and mixtures of these.

This further feature of the invention also comprises co-polymers obtained by esterifying 2-bromo-2-nitropropane-1,3-diol and one or more other diols with the dicarboxylic acid. Examples of other diols which may be used in the preparation of such co-polymers are ethylene glycol, propylene glycol, trimethylene glycol, 1,4-, 1,3- and 2,3-butanediols, diethylene glycol, dipropylene glycol, hexamethylene glycol, neopentyl glycol and 2,2'-dihydroxydiethylsulphide.

The reaction is carried out by known methods, i.e. the diol and the dicarboxylic acid are heated together in the presence of a catalytic amount of a strong acid such as sulphuric acid or p-toluene sulphonic acid under conditions such that the water which is formed in the reaction distils out from the reaction mixture. If desired the reaction may be carried out in a solvent for the diol and the dicarboxylic acid, the water produced in the reaction being distilled out azeotropically with a part of the solvent. The polyester which is formed is isolated from the reaction mixture by known methods, e.g. methods similar to those indicated for the corresponding polyurethane polymers.

The diol and dicarboxylic acid should be employed in approximately equimolecular amounts, but a slight excess of one or the other may be used according to whether it is desired to obtain a hydroxyl-ended or carboxyl ended polymer.

An alternative process for the manufacture of the polyesters comprises a transesterification reaction between a lower alkyl ester of a dicarboxylic acid and 2-bromo-2-nitropropane 1,3-diol.

The transesterification reaction is preferably carried out under conditions such that the lower alkanol which is also formed distils out of the reaction mixture. Suitable lower alkyl esters of dicarboxylic acids for use in the transesterification reaction are lower alkyl esters of those dicarboxylic acids mentioned above. By "lower alkyl" we mean alkyl radicals containing from 1 to 4 carbon atoms. Methyl esters are preferred. The reaction is preferably catalysed by a strong acid as indicated previously. As in the case of direct esterification, one or more other diols may be used together with the 2-bromo-2-nitropropane-1,3-diol in the transesterification reaction.

The polyurethanes and polyesters of the present invention are valuable biocides, and according to a still further feature of the invention there is provided a method for protecting a medium which is susceptible to attack by micro-organisms against such attack, and controlling or preventing the proliferation of micro-organisms in a medium already infected thereby, which comprises adding to the said medium a biocidal amount of a polymer as hereinbefore defined.

In the above definition, preventing the proliferation of micro-organisms means that the micro-organisms are not allowed to multiply further, the number of micro-organisms not necessarily being substantially altered. Controlling the proliferation of micro-organisms means that the rate of multiplication of the micro-organisms is either reduced or rendered negative (i.e. a reduction in numbers, including the case of complete eradication).

The biocides are particularly useful in the treatment of aqueous media, for example, industrial cooling waters, the water systems of paper mills, aqueous oil emulsions such as metal working fluids, water-based paints (i.e. emulsion paints) and water-based adhesives, but they also find application as paint film fungicides and in the prevention of fungal and/or bacterial attack on wood and leather, and are active against algae and yeasts.

The amount of biocide which is used will depend upon the medium which is being treated but for aqueous media an amount from 1 to 1000 parts per million by weight, based on the weight of the medium, is generally effective.

When used as a paint film fungicide the biocidal polymer will generally be used in an amount to provide a concentration in the paint, before its application to a substrate, of from 500 to 10,000 parts per million by weight.

The invention is illustrated but not limited by the following Examples, in which parts and percentages are by weight.

EXAMPLE 1

Preparation of polymeric biocide from 2-bromo-2-nitropropane-1,3-diol and hexamethylene diisocyanate.

11.7 Parts of 2-bromo-2-nitropropane-1,3-diol are suspended in 86 parts of dry toluene. 0.5 Part of dibutyl tin-dilaurate and 0.4 part of triethylamine dissolved in 5 parts of toluene are added to the suspension, and 8.78 parts of hexamethylene diisocyanate a are added portionwise, with constant stirring of the reaction mixture. The temperature of the mixture rises by approximately 4° C. Stirring is continued for a further 10 minutes to ensure that the exotherm is complete. A solid lump of reaction product forms. The reaction mixture is then heated to 60° C. and held at this temperature for 80 minutes. The toluene is decanted from the viscous product while still hot, but contains only an insignificant amount of dissolved material and is discarded. The oily, viscous product is dissolved in acetone and the solvent is removed by distillation under reduced pressure. The solid residue is then dissolved in methanol and the solution is similarly stripped of solvent to give a tacky foam, which on being allowed to stand until the last traces of solvent have evaporated yields a brittle solid. This product softens at 72° C. with subsequent decomposition. Yield 21.1 parts.

EXAMPLE 2

Preparation of polymeric biocide from 2-bromo-2-nitropropane-1,3-diol and diphenylmethane-4,4'-diisocyanate.

11.7 Parts of 2-bromo-2-nitropropane-1,3-diol are suspended in 130 parts of toluene in which are dissolved 0.5 part of dibutyl tin dilaurate and 0.4 part of triethylamine. To this suspension is added during 15 minutes, dropwise and with constant stirring, a solution of 13.06 parts of diphenylmethane-4,4'-diisocyanate in 43 parts of toluene. During the addition an exotherm of 5° C. is observed. On completion of the addition the temperature of the reaction mixture is raised to 60° C. and held at this level for 2 hours. On cooling, a mixture of two solids of different appearance is obtained, which however on subsequent filtration and drying are found to be different physical forms of the same material. The product decomposes at temperatures above 180° C. Yield 13.7 parts.

EXAMPLE 3

Testing of the products of Examples 1 and 2 for antibacterial and antifungal activity.

The above-mentioned products are incorporated into molten nutrient agar and malt agar to give final concentrations in each case of 100 parts per million (ppm) by weight.

The biocide containing agar is poured into Petri dishes and allowed to solidfy. Plates containing each biocide are poured in triplicate.

A microtiter AM 80 Automatic Inoculator is used for inoculating the agar plates. The nutrient agar plates are inoculated with the bacteria *Pseudomonas aeruginosa* (*Ps. aerug*), *Escherichia coli* (*E. coli*) and *Staphylococcus aureus* (*S. aureus*), and the malt agar plates are inoculated with the fungi *Pullularia pullulans* (*P. pullulans*), *Aspergillus niger* (*Asp. nig*), *Cladosporium sphaerospermum* (*Clad.sphaer*), *Alternaria tenuis* (*Alt. ten*) and *Chaetomium globosum* (*Chaet. glob*).

The nutrient agar plates are incubated at 37° C. for 24 hours and the malt agar plates are incubated at 25° C. for 48 hours, after which the plates are examined for the presence or absence of microbial growth.

Results are as follows:

| Biocide (at 100 ppm) | Ps aerug | E coli | S aureus | P pullulans | Asp. nig | Clad sphaer | Alt ten | Chaet glob |
|---|---|---|---|---|---|---|---|---|
| Ex. 1 | − | − | − | − | + | − | − | − |
| Ex. 2 | + | + | + | − | − | − | − | − |

In the above table, + indicates microbial growth and − indicates absence of microbial growth.

These results indicate that both biocides have high antifungal activity and that the biocide of Example 1 also has high antibacterial activity.

EXAMPLE 4

(a) Preparation of a polymeric biocide from 2-bromo-2-nitropropane-1,3-diol and adipic acid.

11.7 Parts of 2-bromo-2-nitropropane-1,3-diol are suspended in 129 parts of dry toluene. 8.5 Parts of adipic acid and 0.5 part of p-toluenesulphonic acid are added to the suspension. The temperature of the mixture is raised to reflux and maintained at this temperature until evolution of water ceases, the water being collected in a Dean and Stark apparatus.

The contents of the reaction vessel are cooled to room temperature and the lower viscous layer is separated from the upper toluene layer, heated in a rotary evaporator to remove most of the volatile contaminants and finally dried to constant weight in a vacuum oven at 50° C. The product is a dark viscous oil, yield 9.3 parts.

If in the above preparation the adipic acid is replaced by an equimolar amount of (b) malonic acid or (c) azelaic acid or (d) maleic anhydride or (e) oxalic acid, all other factors remaining unchanged, then similar polymers are obtained in the following yields:

(b) 8.6 parts
(c) 16.5 parts
(d) 4.4 parts
(e) 7.3 parts

Characterisation of the polymers described in Examples 1, 2 and 4(a)–(e)

Polymer of Example 1—Gel permeation chromatography indicates two molecular weight maxima at approximately 1700 cm and 3500 cm. Infra-red spectroscopy indicates that the material is a polyurethane in that it shows a carbonyl absorption at 1720 cm$^{-1}$. Elemental analysis: C, 35.5%; H, 5.2%, N, 11.0%; Br, 23.5%.

Polymer of Example 2. The infra-red spectrum shows a strong broad carbonyl absorption at 1730 cm$^{-1}$.

Polymer of Example 4(a) The infra-red spectrum indicates that the material is a polyester with a strong, broad carbonyl band at 1730 cm$^{-1}$.

Polymer of Example 4(b) The infra-red spectrum shows a strong, broad carbonyl band at 1710 cm$^{-1}$.

Polymer of Example 4(c) The infra-red spectrum shows a strong, broad carbonyl band at 1740 cm$^{-1}$.

Polymer of Example 4(d) The infra-red spectrum shows a strong, broad carbonyl band at 1705 cm$^{-1}$.

Polymer of Example 4(e) The infra-red spectrum shows a strong, broad carbonyl at 1720 cm$^{-1}$.

EXAMPLE 5

Testing of the products of Example 4 for antibacterial and antifungal activity.

The tests are carried out exactly as described in Example 3. Results are as follows:

| Biocide (at 100 ppm) | Ps aerug | E coli | S aureus | P pullulans | Asp nig | Clad sphaer | Alt ten | Chaet glob |
|---|---|---|---|---|---|---|---|---|
| Ex. 4(a) | − | − | − | − | + | − | − | − |
| Ex. 4(b) | − | − | − | + | + | + | NT | + |
| Ex. 4(c) | − | − | − | − | + | − | NT | − |
| Ex. 4(d) | − | − | − | + | + | + | NT | + |
| Ex. 4(e) | − | − | − | + | + | + | NT | + |

In the above table, + indicates microbial growth, − indicates absence of microbial growth and NT indicates that the compound was not tested against that microorganism.

These results indicate that these polyesters are active against all the bacteria and that the polyadipate (Example 4(a)) and polyazelate (Example 4(c)) are active against certain of the fungi.

EXAMPLE 6

Testing of the products of Examples 1, 4(b), 4(d) and 4(e) for antibacterial activity in metal-working fluid.

A 5% oil-in-water emulsion is prepared by adding Prosol 44 (Mobil) to tap water, and dispensed in 100 ml volumes in 250 ml sterile conical flasks. 1% solutions of the polymers under test are prepared in dimethylformamide and added to the emulsions to give final concentrations of 100 and 200 ppm active ingredient. The control consists of an emulsion containing the equivalent volume of dimethylformamide required to make up the volume of emulsion to 200 ml if biocide had been present.

The 100 ml volumes of emulsions are inoculated with 0.5 ml of a 24 hour broth culture of *Ps.aeruginosa* once weekly for 3 weeks.

The inoculated emulsions are incubated at 30° C. in a rotary shaker (80 revolutions per minute) and each week for 3 weeks at 24 hours and 3 days after inoculation 1 ml samples are removed and surviving bacteria are determined in nutrient agar by the standard decimal dilution procedure.

Results are as follows:

| Treatment | | Survivors (cells/ml emulsion in) | | | | | |
|---|---|---|---|---|---|---|---|
| | | Week 1 | | Week 2 | | Week 3 | |
| | | Day 1 | Day 3 | Day 1 | Day 3 | Day 1 | Day 3 |
| Example 1 | 200 ppm | < 10 | < 10 | < 10 | < 10 | < 10 | < 10 |
| | 110 ppm | < 10 | < 10 | < 10 | < 10 | $1.2 \times 10^3$ | < 10 |
| Example 4(b) | 200 ppm | < 10 | < 10 | < 10 | < 10 | $> 3 \times 10^3$ | < 10 |
| | 110 ppm | < 10 | < 10 | $2.0 \times 10^1$ | < 10 | $> 3 \times 10^5$ | $> 3.0 \times 10^5$ |
| Example 4(d) | 200 ppm | < 10 | < 10 | < 10 | < 10 | < 10 | < 10 |
| | 100 ppm | < 10 | < 10 | $5.5 \times 10^4$ | < 10 | $1.0 \times 10^4$ | $> 3.0 \times 10^5$ |
| Example 4(e) | 200 ppm | < 10 | < 10 | $9.3 \times 10^2$ | < 10 | < 10 | < 10 |
| | 100 ppm | < 10 | < 10 | $1.0 \times 10^2$ | < 10 | $2.0 \times 10^5$ | $> 3.0 \times 10^5$ |
| Control | | $2.2 \times 10^7$ | $2.1 \times 10^7$ | $2.1 \times 10^7$ | $3.7 \times 10^7$ | $>3.0 \times 10^7$ | $4.1 \times 10^7$ |

These results show that the polymers tested have high activity as metal-working fluid biocides.

EXAMPLE 7

Testing of the products of Examples 4(b), 4(c), 4(d) and 4(e) for activity as in-can paint preservatives.

1% solutions of the biocides in dimethylformamide (DMF) are added to 50 g quantities of a styrene-acrylic emulsion paint to give final biocide concentrations of 100 and 200 ppm. The controls consist of paints minus biocide but containing a DMF level equivalent to that required to provide 200 ppm of biocide.

Once weekly for two successive weeks the biocide-containing paints are inoculated with 1 ml of a mixture of *Ps. aeruginosa, E. coli* and *Enterobacter cloacae.* The inoculated paints are incubated at 30° C. and each week 1 and 3 days after inoculation surviving bacteria are determined in the samples by the standard decimal dilution procedure. Results are as follows:

| Treatment | | Survivors (cells/g paint) | | | |
|---|---|---|---|---|---|
| | | Week 1 | | Week 2 | |
| | | Day 1 | Day 3 | Day 1 | Day 3 |
| Example 4(b) | 200 ppm | < 10 | < 10 | $3.5 \times 10^3$ | < 10 |
| | 100 ppm | $5.0 \times 10^4$ | < 10 | $2.0 \times 10^4$ | < 10 |
| Example 4(c) | 200 ppm | < 10 | < 10 | < 10 | < 10 |
| | 100 ppm | < 10 | < 10 | $2.0 \times 10^5$ | $2.5 \times 10^5$ |
| Example 4(d) | 200 ppm | < 10 | < 10 | < 10 | < 10 |
| | 100 ppm | < 10 | < 10 | $5.0 \times 10^4$ | < 10 |
| Example 4(e) | 200 ppm | < 10 | < 10 | < 10 | < 10 |
| | 100 ppm | < 10 | < 10 | < 10 | < 10 |
| Control | | $1.5 \times 10^6$ | $3.0 \times 10^7$ | $2.0 \times 10^7$ | $8.0 \times 10^6$ |

These results show that the polymers tested have high activity as in-can paint preservatives.

EXAMPLE 8

Testing of the products of Examples 1 and 4(a) for antibacterial activity in the presence of wood pulp.

The polymers as 1% solution in DMF are diluted further in sterile distilled water so that an addition of 1 ml volumes of biocide solution to 19 ml of wood pulp medium (comprising glucose 10 g, bacteriological peptone 5 g, milled mechanical wood pulp 2.5 g and water 1 liter), final biocide concentrations of 5, 10, 20, 50 and 100 ppm are obtained.

The biocide-containing wood pulp media are inoculated with 0.1 ml of a 1:1:1 mixture of broth cultures of *Ps. aeruginosa, Bacillus subtilis* and *E.cloacae.*

After 48 hours incubation at 30° C. the media are examined for the presence or absence of bacterial growth, after which they are reinoculated.

Results are as follows:

| Treatment | Minimal Inhibitory Concentration (ppm) after | |
|---|---|---|
| | 1st Inoculation | 2nd Inoculation |
| Example 1 | 50 | 50 |
| Example 4(a) | 20 | 20 |

These results indicate that the biocides retain high activity in the presence of wood pulp and are therefore suitable for use as paper mill slimicides.

EXAMPLE 9

Testing of the product of Example 1 for activity against a yeast.

The polymer is added to 100 ml volumes of sterile distilled water in 250 ml conical flasks to give concentrations of 100, 50, 25 and 10 ppm. The control consists of 100 ml of distilled water.

Each biocide solution is inoculated with 1 ml of a 3 day culture of the yeast *Margarinomyces luteo-viridis* and incubated at 30° C. on an orbital shaker.

After incubation periods of 2, 4, 6 and 24 hours, 1 ml samples are removed from each flask and surviving yeast cells are determined on malt agar using the standard decimal dilution procedure.

Results are as follows:

| Treatment | | Survivors (cells/ml) after | | | |
|---|---|---|---|---|---|
| | | 2 hours | 4 hours | 6 hours | 24 hours |
| Example 1 | 100 ppm | <10 | <10 | <10 | <10 |
| | 50 ppm | $1.0 \times 10^2$ | <10 | <10 | <10 |
| | 25 ppm | $4.4 \times 10^3$ | $3.0 \times 10^1$ | <10 | <10 |
| | 10 ppm | $2.2 \times 10^5$ | $2.0 \times 10^3$ | <10 | <10 |
| Control | | $2.18 \times 10^8$ | $1.71 \times 10^8$ | $1.00 \times 10^8$ | $9.60 \times 10^7$ |

These results show that the polymer has high activity against yeasts.

We claim:
1. Polyurethane polymers having the general formula:

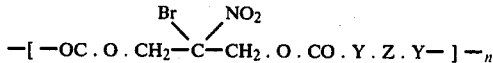

wherein each Y is an —NH— group, Z is an optionally substituted divalent hydrocarbon radical and n is an integer of at least 2.

2. A process for the manufacture of the polymers claimed in claim 1 which comprises reacting together 2-bromo-2-nitropropane-1,3-diol and a diisocyanate $Z(NCO)_2$ wherein Z has the meaning stated in claim 1.

3. A process as claimed in claim 2 wherein the 2-bromo-2-nitropropane-1,3-diol is used in slight molar excess over the diisocyanate.

4. A method for protecting a medium which is susceptible to attack by micro-organisms against such attack, and controlling or preventing the proliferation of micro-organisms in a medium already infected thereby, which comprises adding to the said medium a biocidal amount of a polymer as claimed in claim 1.

5. A method as claimed in claim 4 wherein the medium is an aqueous medium and the polymer is employed in an amount from 1 to 1000 parts per million by weight based on the weight of the aqueous medium.

6. A method as claimed in claim 4 wherein the medium is a paint film and the polymer is employed in an amount from 500 to 10,000 parts per million by weight based on the weight of paint before its application to a substrate.

7. Media which are susceptible to attack by micro-organisms, protected against such attack by the method claimed in claim 4.

8. A polymer according to claim 1 wherein Z is hexamethylene or p-$C_6H_4CH_2C_6H_4$-p.

9. A process according to claim 2 wherein the diisocyanate is hexamethylene diisocyanate or diphenylmethane-4,4'-diisocyanate.

* * * * *